United States Patent [19]
Bleck et al.

[11] Patent Number: 5,530,177
[45] Date of Patent: Jun. 25, 1996

[54] TRANSGENIC MICE PRODUCING BOVINE α-LACTALBUMIN IN THEIR MILK

[75] Inventors: Gregory T. Bleck, Madison; Robert D. Bremel, Waunakee, both of Wis.

[73] Assignee: Wisconsin Milk Marketing Board, Madison, Wis.

[21] Appl. No.: 71,601

[22] Filed: Jun. 4, 1993

Related U.S. Application Data

[63] Continuation of Ser. No. 744,765, Aug. 13, 1991, abandoned.

[51] Int. Cl.$^6$ .......................... C12N 5/00; C12N 15/00; C12N 15/63; C07H 21/04
[52] U.S. Cl. ..................... 800/2; 435/172.3; 435/320.1; 435/69.1; 536/24.1
[58] Field of Search .............................. 800/2; 536/24.1; 435/320.1, 69.1

[56] References Cited

PUBLICATIONS

Lee (1988) Nucleic Acids Res. 16, 1027–1041.
Vilotte et al (1989) Eu J. Biochem 186, 43–48.
Stormont (1982) JAVMA 181, 1120–1124.
Akers, R. M. et al., 1981, "Prolactin regulation of milk secretion and biochemical differentiation of mammary epithelial cells in periparturient cows." *Endocrinology*, 109:23–30.
Alberts, B. et al., 1989, *Molecular Biology of The Cell* (Second Edition), Garland Publishing, Inc., New York, pp. 265–271.
Bonsing, J. et al., 1988, "Complete nucleotide sequence of the bovine beta–casein gene," *Aust. J. Biol. Sci.*, 41: 527–37.
Brew, K. and R. L. Hill, 1975, "Lactose biosynthesis." *Rev. Physiol. Biochem. Pharmacol.*, 72:105–58.
Eigel, W. N. et al., 1984, "Nomenclature of proteins of cow's milk: fifth revision." *J. Dairy Sci.*, 67:1599–1631.
Goodman, G. T. et al., 1983, "Hormonal regulation of alpha–lactalbumin secretion from bovine mammary tissue cultured in vitro." *Endocrinology*, 112:1324–30.
Hall, L., et al., 1987, "Organization and sequence of the human α–lactalbumin gene," *Biochem. J.*, 242:735–42.
Hurley, W. L. and L. A. Schuler, 1987, "Molecular cloning and nucleotide sequence of a bovine α–lactalbumin cDNA," *Gene*, 61:119–22.
Larson, B. L., 1985, "Biosynthesis and cellular secretion of milk." In: *Lactation*, pp. 129–163, edited by B. L. Larson, The Iowa State University Press, Ames.
Lewin, B., 1990, *Genes IV*, Oxford University Press, New York, pp. 691–702.
McFadden, T. B. et al., 1987, "Alpha–lactalbumin in bovine serum: relationships with udder development and function." *J. Dairy Sci.*, 70:259–64.
Vilotte, J. et al., 1987, "Complete nucleotide sequence of bovine α–lactalbumin gene: comparison with its rat counterpart." *Biochimie*, 69: 609–20.
Woychik, R., et al., 1982, "Cloning and nucleotide sequencing of the bovine growth hormone gene." *Nucl. Acids Res.*, 10:7197–7210 (1982).

*Primary Examiner*—Jacqueline M. Stone
*Assistant Examiner*—Deborah Crouch
*Attorney, Agent, or Firm*—DeWitt Ross & Stevens

[57] ABSTRACT

The present invention relates to the use of a mammary specific α-lactalbumin regulatory sequence to assist in the production of recombinant proteins in mammals' milk. The invention also relates to the genetically engineered mammal that produces the desired recombinant product in its milk and to the products produced by the genetically engineered mammal, including the altered composition of milk and the semen which includes the desired α-lactalbumin protein DNA sequence.

7 Claims, 13 Drawing Sheets

```
1     GATCAGTCCT  GGGTGGTCAT  TGAAAGGACT  GATGCTGAAG  TTGAAGCTCC  AATACTTTGG
      CCACCTGATG  CGAAGAACTG  ACTCATGTGA  TAAGACCCTG

101   ATACTGGGAA  AGATTGAAGG  CAGGAGGAGA  AGGGATGACA  GAGGATGGAA  GAGTTGGATG
      GAATCACCAA  CTCGATGGAC  ATGAGTTTGA  GCAAGCTTCC

201   AGGAGTTGGT  AATGGGCAGG  GAAGCCTGGC  GTGCTGCAGT  CCATGGGGTT  GCAAAGAGTT
      GGACACTACT  GAGTGACTGA  ACTGAACTGA  TAGTGTAATC

301   CATGGTACAG  AATATAGGAT  AAAAAAGAGG  AAGAGTTTGC  CCTGATTCTG  AAGAGTTGTA
      GGATATAAAA  GTTTAGAATA  CCTTTAGTTT  GGAAGTCTTA

401   AATTATTTAC  TTAGGATGGG  TACCCACTGC  AATATAAGAA  ATCAGGCTTT  AGAGACTGAT
      GTAGAGAGAA  TGAGCCCTGG  CATACCAGAA  GCTAACAGCT

501   ATTGGTTATA  GCTGTTATAA  CCAATATATA  ACCAATATAT  TGGTTATATA  GCATGAAGCT
      TGATGCCAGC  AATTTGAAGG  AACCATTTAG  AACTAGTATC

601   CTAAACTCTA  CATGTTCCAG  GACACTGATC  TTAAAGCTCA  GGTTCAGAAT  CTTGTTTTAT
      AGGCTCTAGG  TGTATATTGT  GGGGCTTCCC  TGGTGGCTCA

701   GATGGTAAAG  TGTCTGCCTG  CAATGTGGGT  GATCTGGGTT  CGATCCCTGG  CTTGGGAAGA
      TCCCCTGGAG  AAGGAAATGG  CAACCCACTC  TAGTACTCTT

801   ACCTGAAAAA  TTCCATGGAC  AGAGGAGCCT  TGTAAGCTAC  AGTCCATGGG  ATTGCAAAGA
      GTTGAACACA  ACTGAGCAAC  TAAGCACAGC  ACAGTACAGT

901   ATACACCTGT  GAGGTGAAGT  GAAGTGAAGG  TTCAATGCAG  GGTCTCCTGC  ATTGCAGAAA
      GATTCTTTAC  CATCTGAGCC  ACCAGGGAAG  CCCAAGAATA

1001  CTGGAGTGGG  TAGCCTATTC  CTTCTCCAGG  GGATCTTCCC  ATCCCAGGAA  TTGAACTGGA
      GTCTCCTGCA  TTTCAGGTGG  ATTCTTCACC  AGCTGAACTA

1101  CCAGGTGGAT  ACTACTCCAA  TATTAAAGTG  CTTAAAGTCC  AGTTTTCCCA  CCTTTCCCAA
      AAAGGTTGGG  TCACTCTTTT  TTAACCTTCT  GTGGCCTACT

1201  CTGAGGCTGT  CTACAAGCTT  ATATATTTAT  GAACACATTT  ATTGCAAGTT  GTTAGTTTTA
      GATTTACAAT  GTGGTATCTG  GCTATTTAGT  GGTATTGGTG

1301  GTTGGGGATG  GGGAGGCTGA  TAGCATCTCA  GAGGGCAGCT  AGATACTGTC  ATACACACTT
      TTCAAGTTCT  CCATTTTTGT  GAAATAGAAA  GTCTCTGGAT

1401  CTAAGTTATA  TGTGATTCTC  AGTCTCTGTG  GTCATATTCT  ATTCTACTCC  TGACCACTCA
      ACAAGGAACC  AAGATATCAA  GGGACACTTG  TTTTGTTTCA

1501  TGCCTGGGTT  GAGTGGGCCA  TGACATATGA  TGATGTACAG  TCCTTTTCCA  TATTCTGTAT
      GTCTCTAAGA  GGAAGGAGGA  GTTGGCCGTG  GACCCTTTGT

1601  GCATTTTCTG  ATTGCTTCAC  TTGTATTACC  CCTGAGGCCC  CCTTTGTTCC  TGAAATAGGT
      TGGGCACATC  TTGCTTCCTA  GAACCAACAC  TACCAGAAAC

1701  AACATAAATA  AAGCCAAATG  GGAAACAGGA  TCATGTTTGT  AACACTCTTT  GGGCAGGTAA
      CAATACCTAG  TATGGACTAG  AGATTCTGGG  GAGGAAAGGA

1801  AAAGTGGGGT  GAAATTACTG  AAGGAAGCTC  AATGTTTCTT  TGTTGGTTTT  ACTGGCCTCT
      CTTGTCATCC  TCTTCCTGGA  TGTAAGGCTT  GATGCCAGGG

1901  CCCCTAAGGC  TTTTTCCACA  AATAAAAGGA  GGTGAGCAGT  GTGGTGACCC  CATTTCAGAA
      TCTTGAGGGG  TAACCAAAAT  GATGTCCTTT  GTCTCTCTGC

2001  TCCTGGTAGG  CATCCTATTC  CATGCCACCC  AGGCTGAACA  GTTA
```

SEQ ID NO:3

FIG. 5

```
Bovine (Our Sequence) [-546]-[-533]:  CATATTCTATT.CTA  (SEQ ID NO:4)
                                      ||||||||||*|||
Human (Hall) [-587]-[-574]:           CATATTCTATTCCTA  (SEQ ID NO:5)
                                      ||||||||||#|||
Bovine (Vilotte) [-547]-[-533]:       CATATTCTATTTCTA  (SEQ ID NO:6)

Bovine (Our Sequence) [-18]-[-1]:     TCTTGAGGGGTAACCAAA  (SEQ ID NO:7)
                                      |||||*|||||||*||||
Human (Hall) [-17]-[-1]:              TCTTG.GGGGTAGCCAAA  (SEQ ID NO:8)
                                      |||||#||||||##||||
Bovine (Vilotte) [-18]-[-1]:          TCTTGGGGGGTCACCAAA  (SEQ ID NO:9)
```

FIG. 7

TRANSGENIC MICE PRODUCING BOVINE α-LACTALBUMIN IN THEIR MILK

This is a continuation of application Ser. No. 07/744,765 filed Aug. 13, 1991, abandoned.

FIELD OF THE INVENTION

The present invention relates generally to a DNA sequence encoding bovine α-lactalbumin and to methods of producing proteins including recombinant proteins in the milk of lactating genetically engineered or transgenic mammals. The present invention relates also to genetically engineered or transgenic mammals that secrete the recombinant protein. The present invention is also directed to a genetic marker for identifying animals with superior milk producing characteristics.

REFERENCE TO CITED ART

Reference is made to the section preceding the claims for a full bibliography citation of the art cited herein.

DESCRIPTION OF THE PRIOR ART

α-Lactalbumin is a major whey protein found in cow's milk (Eigel et al., 1984). The term "whey protein" includes a group of milk proteins that remain soluble in "milk serum" or whey after the precipitation of casein, another milk protein, at pH 4.6 and 20° C. α-Lactalbumin has these characteristics.

α-Lactalbumin is a secretory protein that normally comprises about 2.5% of the total protein in milk. α-Lactalbumin has been used as an index of mammary gland function in response to hormonal regulation in bovine explant culture (Akers et al., 1981; Goodman et al., 1983) and as an index of udder development (McFadden et al., 1986). α-Lactalbumin interacts with galactosyl transferase and therefore plays an essential role in the biosynthesis of milk sugar lactose (Brew, K. and R.L. Hill, 1975). Lactose is an important component in milk, and contributes to milk osmolality. It is the most constant constituent in cow's milk (Larson, 1985). α-Lactalbumin is useful as an index of lactogenesis in cultured mammary tissue (McFadden et al., 1987). It is therefore believed that α-Lactalbumin is an important protein in controlling milk yield and can be used as an indicator of mammary function.

The expression of bovine α-lactalbumin may be a potential rate limiting process in dairy cattle. If greater expression of the α-lactalbumin gene can be obtained, then more milk and milk protein could be produced. In other words, α-lactalbumin is a potential Quantitative Trait Locus (QTL).

SUMMARY OF THE INVENTION

One object of the present invention is to detect possible genetic differences in the expression of bovine α-lactalbumin.

Another object of the present invention is to provide a DNA sequence encoding a mammary specific bovine α-lactalbumin protein having a specified nucleotide sequence, It is also an object of the present invention to provide a method for genetically engineering the incorporation of one or more copies of a construct comprising an α-lactalbumin control region, which construct is specifically activated in the mammary tissue.

These objects and others are addressed by the present invention, which is directed to a DNA sequence encoding bovine α-lactalbumin having a specified nucleotide sequence.

The present invention is also directed to an expression vector comprising this DNA sequence. Further, the present invention is directed to the protein α-lactalbumin having the nucleotide sequence.

The present invention is also directed to an expression system comprising a mammary specific α-lactalbumin control region which, when genetically incorporated into a mammal, permits the female species of that mammal to produce the desired recombinant protein in its milk.

The present invention is also directed to a genetically engineered or transgenic mammal comprising the specified DNA sequence encoding bovine α-lactalbumin.

The present invention is also directed to a DNA sequence coding for α-lactalbumin, which is operatively linked to an expression system coding for a mammary-specific α-lactalbumin protein control, or any control region which specifically activates α-lactalbumin in milk or in mammary tissue, through a DNA sequence coding for a signal peptide that permits secretion and maturation of the α-lactalbumin in the mammary tissue.

The present invention is also directed to a process for genetically engineering the incorporation of one or more copies of a construct comprising an α-lactalbumin control region which specifically activates α-lactalbumin in milk or in mammary tissue. The control region is operatively linked to a DNA sequence coding for a desired recombinant protein through a DNA sequence coding for a signal peptide that permits the secretion and maturation of α-lactalbumin in the mammary tissue.

The present invention is also directed to a process for the production and secretion into a mammal's milk of an exogenous recombinant protein. The steps include producing milk in a genetically engineered or transgenic mammal. The milk is characterized by an expression system comprising α-lactalbumin control region. The control region is operatively linked to an exogenous DNA sequence coding for the recombinant protein through a DNA sequence coding for a signal for the peptide effective in secreting and maturing the recombinant protein in mammary tissue. The milk is then collected for use. Alternatively, the exogenous recombinant protein is isolated from the milk.

The present invention is also directed to a selection characteristic for identifying superior milk and milk protein producing animals comprising a DNA sequence encoding bovine α-lactalbumin and having a specified nucleotide sequence.

The present invention is also directed to a selection characteristic for identifying superior milk and milk protein producing mammals. The mammals are characterized by inherited genetic material in the DNA structure of the mammal. The genetic material encodes at least one desired dominant selectable marker for bovine α-lactalbumin. One such marker is adenosine, which is located at the −13 position on the control region of the DNA sequence for α-lactalbumin. The present invention is also directed to a method of predicting superior milk and milk protein production in animals comprising identifying the selection characteristic discussed above.

The present invention is further directed to a method for modifying the milk composition in mammals which comprises inserting a DNA sequence encoding bovine α-lactalbumin having a specified nucleotide sequence.

The DNA sequence and the various methods of using it have potentially beneficial uses for dairy farmers, artificial insemination organizations, genetic marker companies, and embryo transfer and cloning companies, to name a few.

The uses for this genetic marker include the identification of superior nuclear transfer embryos and the identification of superior embryos to clone.

The present invention also will aid in the progeny testing of sires. The specified DNA sequence can be used as a genetic marker to identify possible elite sires in terms of milk production and milk protein production. This will increase the reliability of buying superior dairy cattle.

The present invention also will provide assistance in farm management decisions, such as sire selection and selective culling. The physiological markers assist in determining future production performance in addition to a cow's pedigree. From this information, one could buy or retain a heifer with a DNA sequence encoding α-lactalbumin of the present invention and consider culling a heifer without the proper sequence.

BRIEF DESCRIPTION OF THE DRAWINGS

FIG. 5 depicts the nucleotide sequence (SEQ ID NO:3) of the control/enhancer region of the bovine α-lactalbumin protein.

FIG. 7 illustrates a sequence comparison between humans and bovine genes in the 5' flanking region of the bovine α-lactalbumin protein between the present invention U.S. bovine sequence (SEQ ID NO:4), a human sequence (SEQ ID NO:5) and the French bovine (SEQ ID NO:6) for the putative steroid response element and between the present invention U.S. bovine sequence (SEQ ID NO:7), a human sequence (SEQ ID NO:8) and the French bovine (SEQ ID NO:9) for the RNA polymerase binding region, surrounding three of the four nucleotide sequence variant mutations.

DETAIL DESCRIPTION OF THE PREFERRED INVENTION

In the Description the following terms are employed:

Genetic engineering, manipulation or modification: the formation of new combinations of materials by the insertion of nucleic acid molecules produced outside the cell into any virus, bacterial plasmid or other vector system so as to allow their incorporation into a host organism in which they do not naturally occur, but in which they are capable of continued propagation at least throughout the life of the host organism. Although the term incorporates transgenic alteration, the manipulation of the genomic sequence does not have to be permanent, i.e., the genetic engineering can affect only the animal which was directly manipulated.

Transgenic animals: permanently genetically engineered animals created by introducing new DNA sequences into the germ line via addition to the egg.

It is within the scope of the present application to use any mammal for the invention. Examples of mammals include cows, sheep, goats, mice, oxen, camels, water buffaloes, llamas and pigs. Preferred mammals include those that produce large volumes of milk and have long lactating periods.

The present invention is directed to a gene which encodes bovine α-lactalbumin. This gene has been isolated and characterized. The 5' flanking region of the gene has been cloned into six vectors for use as a mammary specific control region in the production of genetically engineered mammals. To better understand the regulation of this control region, 2.0 kilobases of the 5' flanking sequence have been sequenced. The α-lactalbumin 5' flanking sequence serves as a useful mammary-specific "control/enhancer complex" for engineering genetic constructs that could be capable of driving the expression of novel and useful proteins in the milk of genetically engineered or transgenic mammals. This results in an increase in milk production and the protein composition in milk, a change in the milk and/or protein composition in milk, and the production of valuable proteins in the milk of genetically engineered or transgenic mammals. Such proteins include insulin, growth hormone, growth hormone releasing factor, somatostatin, tissue plasminogen activator, tumor necrosis factor, lipocortin, coagulation factors VIII and IX, the interferons, colony stimulating factor, the interlukens, urokinise, industrial enzymes such as cellulases, hemicellulases, peroxidases, and thermal stable enzymes.

The α-lactalbumin gene is the preferred gene for use in the process because it is a mammary specific protein 5' control region. It also exerts the tightest lactational control of all milk proteins. Further, it is independently regulated from other milk proteins and is produced in large quantity by lactating animals.

Total Sequence

Figure 1:
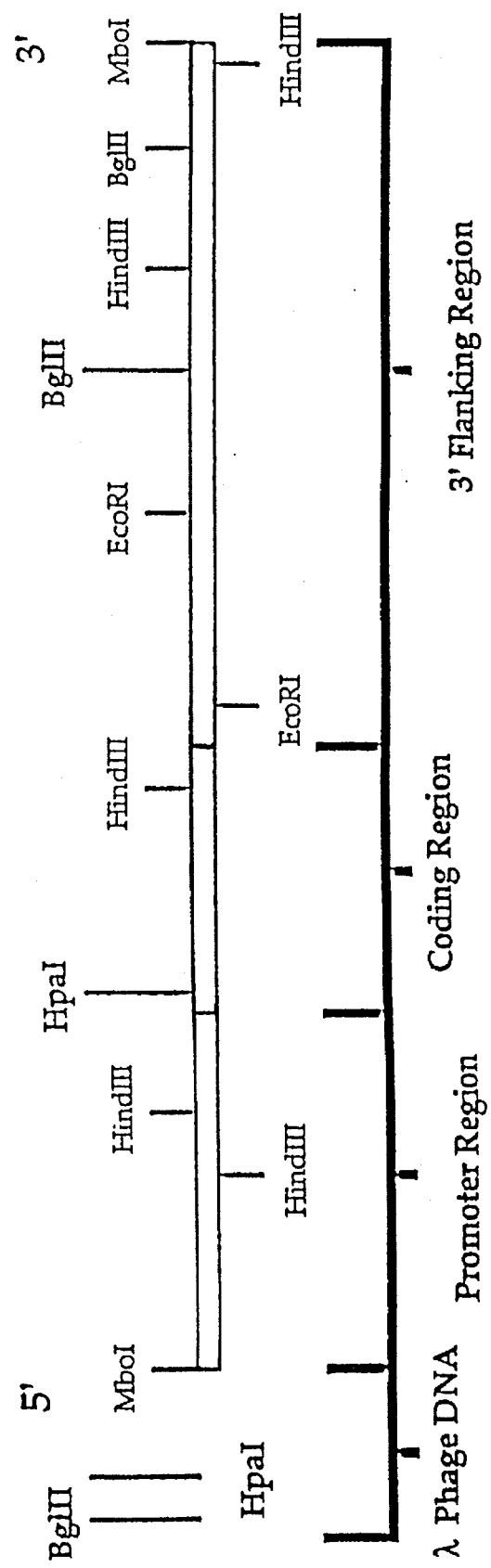
FIG. 1 is a schematic illustration of a partial restriction map of the bovine α-lactalbumin of the present invention. The sequence contains 2.0 kilobases of a 5' flanking region, 1.7 kilobases of a coding region and 8.8 kilobases of a 3' flanking region. Digestion with the Hpa I yields a 2.8 kilobase fragment containing the whole 5' flanking region.

A gene encoding the milk protein bovine α-lactalbumin was isolated from a bovine genomic library (Woychik, 1982). The Charon 28 lambda library was probed using a bovine α-lactalbumin cDNA (Hurley, 1987) and a 770 base pair α-lactalbumin polymerase chain reaction product. The positive lambda clone includes 12.5 kilobases of inserted bovine sequence, consisting of 2.0 kilobases of a 5' flanking (control/enhancer) region, a 1.7 kilobase coding region and 8.8 kilobases of a 3' flanking region. A partial restriction map of the clone is illustrated in FIG. 1.

A 2.8 kilobase Hpa I fragment including the 2.0 kilobase control region along with the signal peptide coding region was cloned into the EcoRV site of the plasmid pIC 20R. The plasmid is illustrated in schematic outline in FIG. 2.

Figure 4:
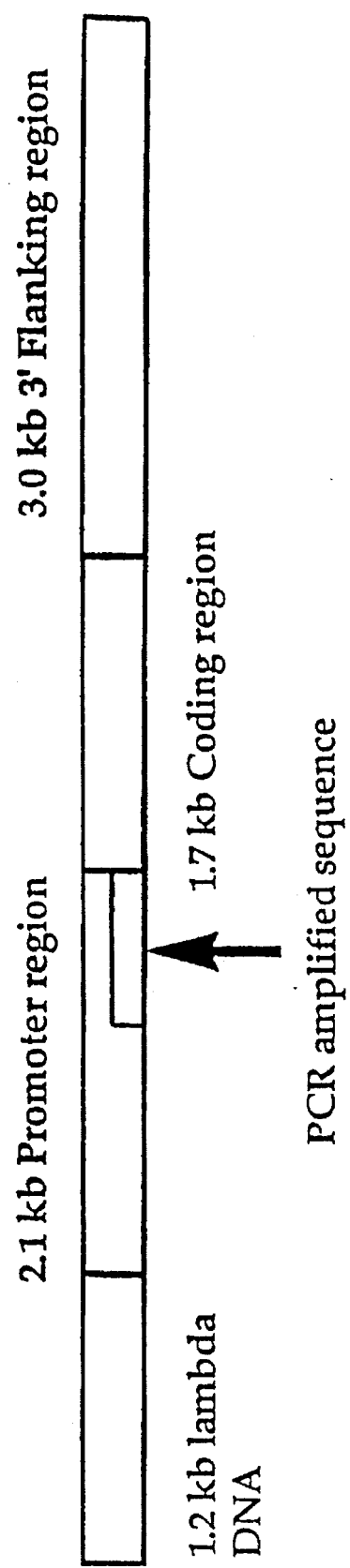
FIG. 4 is a schematic illustration of a detailed map of the 8.0 kilobase BglII fragment.

An 8.0 kilobase Bgl II fragment containing a 2.0 kilobase 5' flanking control region, a 1.7 kilobase coding region, 3.0 kilobases of a 3' flanking region, 1.2 kilobases of a lambda DNA has also been isolated. Reference is made to FIG. 4 for a map of the 8.0 kilobase fragment. Transgenic mice have been produced using the Bgl II fragment.

Control/Enhancer Region

Figure 2:
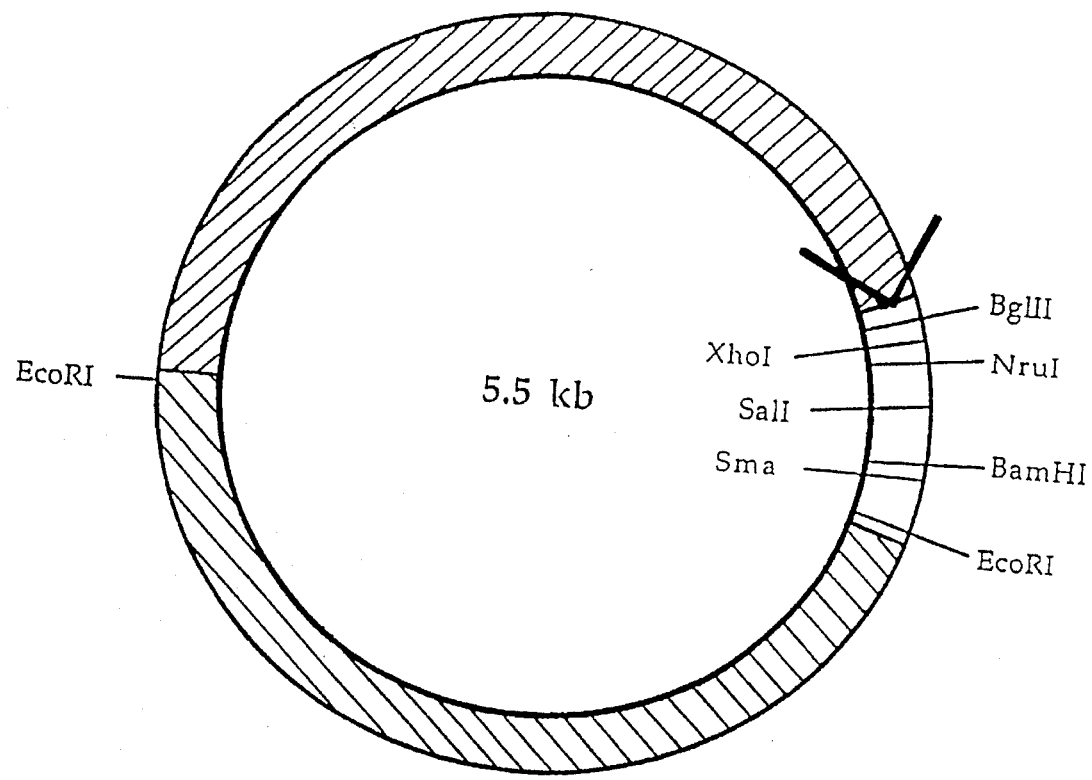
FIG. 2 depicts in schematic outline a map of the plasmid A-lac Pro/pIC 20R. A Hpa I fragment of the genomic clone was inserted into the EcoRV site of pIC 20R. The Hpa I fragment contains 2.1 kb of 5' flanking DNA the signal peptide coding region of α-lactalbumin and 8 bases encoding the mature α-lactalbumin protein. Six unique enzyme sites are available for attaching various genes to the sequence.
Figure 3:
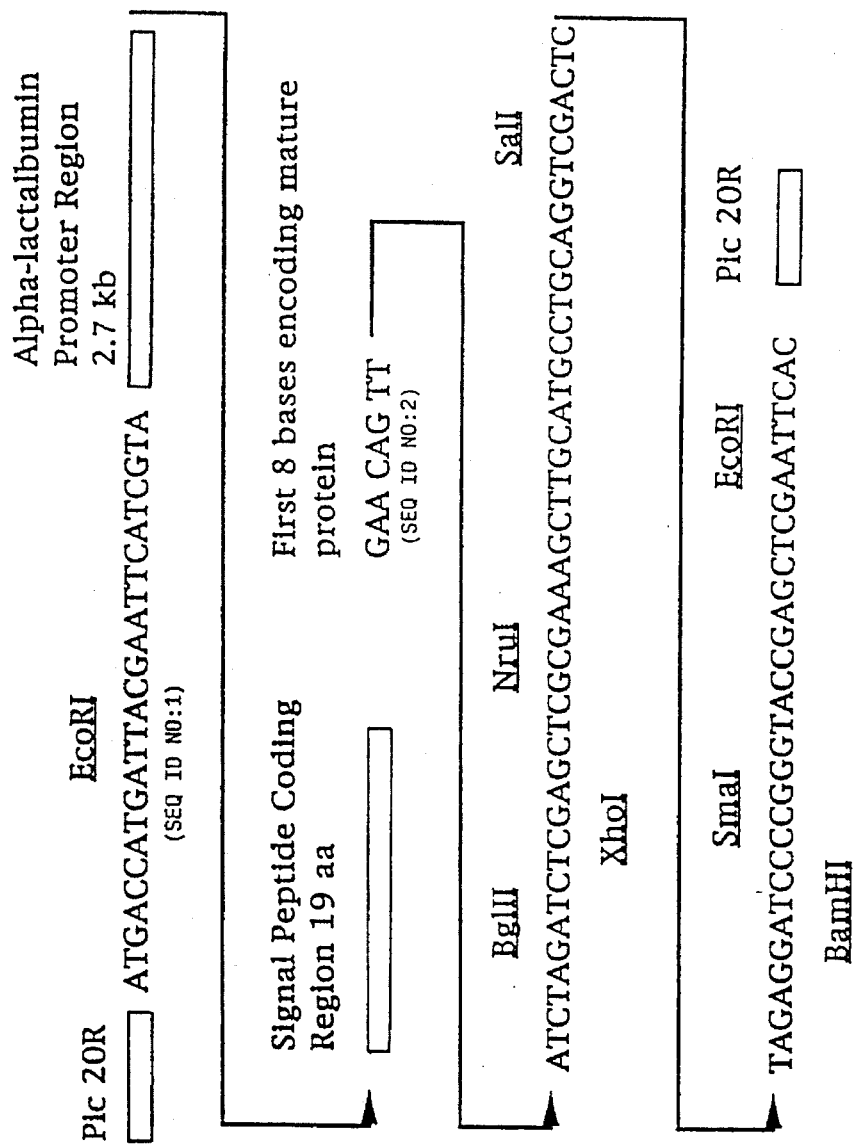
FIG. 3 is a schematic illustration of a detailed map of the α-lactalbumin 5' flanking control region cloned in EcoRV site of the plasmid pIC 20R (SEQ ID NO:1, SEQ ID NO:2).

The 2.0 kilobase 5' flanking region has been cloned into the vectors Pic 20R and Bluescript KS+. A schematic illustration of the α-lactalbumin 5' flanking control region cloned in the EcoRV site of pIC 20R is depicted in FIGS. 2 and 3 (SEQ ID NO:1, SEQ ID NO:2).

The construct's multiple cloning site, which exists downstream of the signal peptide coding region, permits various genes to be attached to the α-lactalbumin control region. Thus, this vector allows for easy attachment of specific coding sequences of genes. It contains all elements necessary for expression of proteins in milk, i.e., a mammary specific control region, a mammary specific signal peptide coding region and a mature protein-signal peptide splice site which is able to be cleaved in the mammary gland. The vector also contains many unique restriction enzyme sites for ease of cloning. Attachment of genes to this control region will allow for mammary expression of the genes when these constructs are placed into mammals. These vectors also contain the α-lactalbumin signal peptide coding sequence which will allow for proper transport of the expressed protein into the milk of the lactating mammal.

Figure 6:
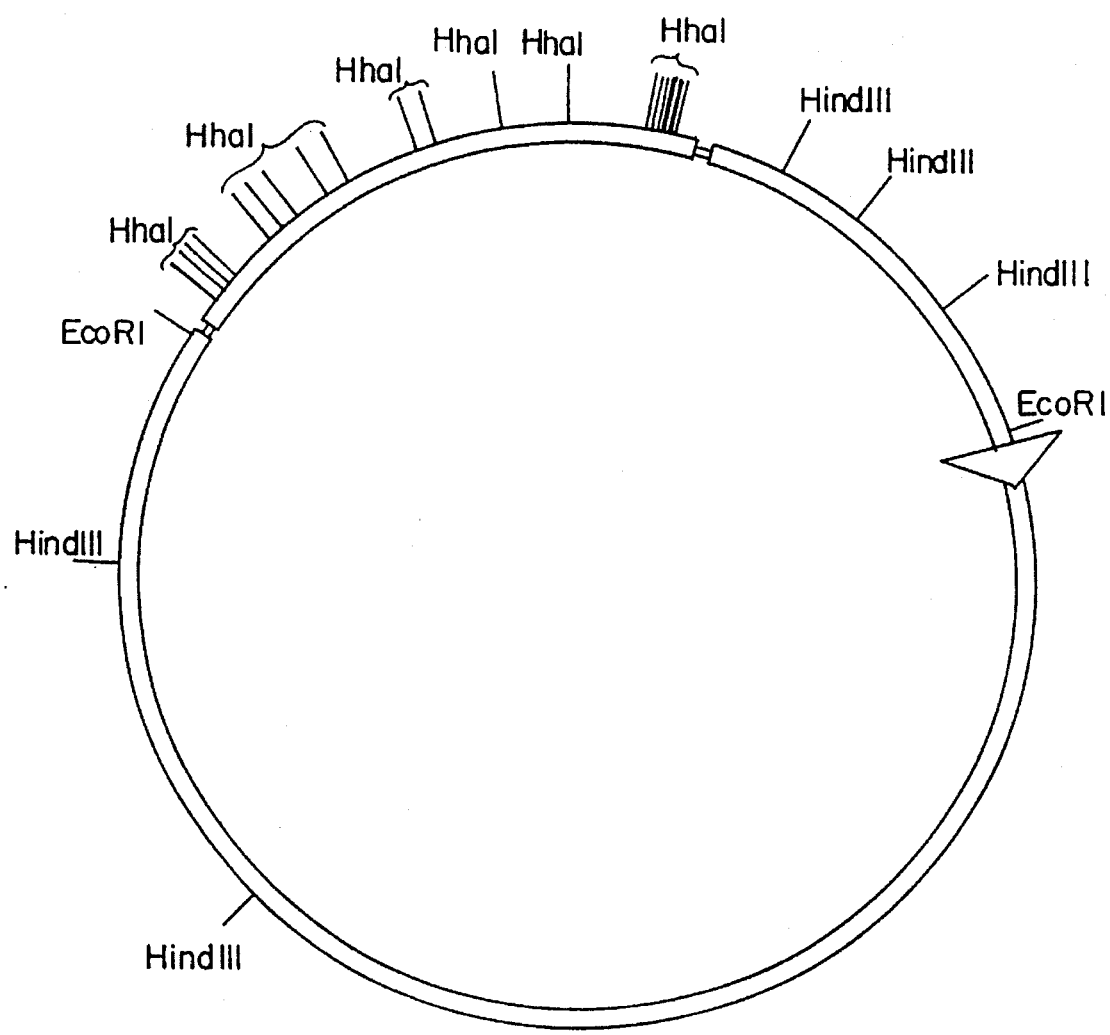
FIG. 6 depicts in schematic outline a map of a plasmid containing bovine α-lactalbumin-bovine β-casein gene construct.

The constructs containing the control region have driven mammary expression of desired proteins in transgenic mice. Bovine α-lactalbumin levels of greater than 1 mg/ml have been observed in the milk of transgenic mouse lines as described in Example 2 (infra.). Constructs containing the 2.0 kilobase region attached to the bovine β-casein gene (Bonsing, J., et al., 1988) as well as the bacterial reporter gene chloramphenicol acetyl transferase have been produced in our lab. FIG. 6 is a schematic representation of a plasmid containing the bovine α-lactalbumin bovine B-casein gene construct. The genomic DNA sequence containing the bovine B-casein gene was attached to the 5' flanking sequence of the bovine α-lactalbumin 5' flanking sequence. The vector contains the polyadenylation site of B-casein along with approximately 100 base pairs of 5' flanking DNA. The 100 base pairs of 5' flanking DNA are attached to the bovine α-lactalbumin 5' flanking region at the −100 position. The construct uses the proximal promoter elements of β-casein and the distal control region elements of α-lactalbumin. The β-casein construct has been used to produce transgenic mice as is illustrated in the examples.

To understand the control of the control/enhancer region the 2.0 kilobases of 5' flanking region were sequenced. A single strand copy of the sequence is listed in FIG. 5 (SEQ ID NO:3). The sequence is listed 5' to 3= with the signal peptide coding region underlined.

Regulatory Sequences

Potential regulatory sequences contained within the 5'-flanking region of bovine α-lactalbumin have been identified. There are possible regulatory regions in the introns as well as in the 3' flanking region. Portions of the suspected control regions were examined for possible sequence differences in the population which might be related to milk and milk protein production of individual cows. The differences in the regulatory regions of α-lactalbumin are expected to lead to differences in expression of α-lactalbumin mRNA. The increased cellular content of mRNA will increase the expression of α-lactalbumin protein with a concomitant increase in lactose synthase resulting, ultimately, in a milk and milk protein production increase. This type of mechanism would be considered a major gene effect on milk and milk protein production by α-lactalbumin. The changes are viewed as causally-linked to changes in milk and milk protein production and not correlatively-linked. Correlatively-linked traits are those which are closely associated with an unknown genetic loci which has the direct impact on the quantitative trait.

Sequence differences between the U.S. Holstein and the French cow (Vilotte, et al., 1987) of an unknown breed were found at four positions within the 5' flanking region. One of the identified sequences has a sequence which would indicate that it was asteroid hormone response element. Two other differences were noted in the RNA polymerase binding region and a fourth in the signal peptide coding region of the gene. Because of the relationship between these sequences and known control sequences of mammalian genes, all the variations occur in regions one would expect to be involved in regulation of the amount of mRNA produced. Further, genetic variations which occur in factors binding to these regions would also be expected to cause changes.

FIG. 7 illustrates sequence variants observed in the 5' flanking region between the present invention U.S. bovine, human (Hall et al., 1987) and the French bovine (Vilotte, 1987) for the putative steroid response element (SEQ ID NO:4, SEQ ID NO:5 and SEQ ID NO:6 respectively) and for the RNA polymerase binding region (SEQ ID NO:7, SEQ ID NO:8, and SEQ ID NO:9 respectively). All of the differences occur in highly conserved portions of the gene as seen by comparing this region to the same region of the human α-lactalbumin gene. FIG. 7 also shows that the positions where the bovine genes differ are the same positions the human gene differs from the bovine. These data indicate that the bases are part of a potentially important control region.

A method has been devised to give a clearcut differentiation between two of the variants at a position −13 bases from the start of translation, i.e., 13 base positions from the signal peptide coding region. The two variants are termed (α-Lac (−13) A) and (—Lac (−13) B). The α-lac (−13) A genotype is adenine base at position −13 the α-lac (−13) B genotype is either a guanine, thymine or cytosine base at −13. They can be differentiated with a simple restriction enzyme digest of an amplified polymerase chain reaction (PCR) product using a specific restriction enzyme (MnlI). Because of the specificity of the restriction enzyme MnlI, the restriction analysis is unable to distinguish between these different possibilities. The α-lac (−13) A allele contains an extra MnlI site at position −13 giving the smaller band observed on the gel.

To amplify the appropriate region of DNA, oligonucleotides which frame the sequence of interest were synthesized. These oligonucleotides were chosen because of their specific chemical characteristics. These oligonucleotides were then used in a polymerase chain reaction to amplify the framed portion of the α-lactalbumin gene. The oligonucleotides have the following sequences:

α-lac Seq. 1 (SEQ ID NO:10)
5'ACGCTTGTAAAACGACGGCCAGTTGATTCTCAGTCTCTGTGGT 3'

α-lac Seq. 2 (SEQ ID NO:11)
5'AGCATCAGGAAACAGCTATGACCTGGGTGGCATGGAATAGGAT 3'

Restriction fragment analysis (Sambrook, J. et al., 1989) was used to examine animals from a number of breeds of cattle. In most breeds, namely, Jersey, Guernsey, Brown Swiss, Simmental and Brahman, only one of two genotypes is found. This is the α-lac (−13) B genotype. However, in the most popular and highest milk producing breed of cattle, the Holstein, two genotypes occur at this position. The frequency of the A genotype was 27% in random samples, while the frequency of the B genotype was 73%. Holsteins contain both the genotype found in the other breeds as well as a separate distinct genotype which appears to have arisen within the last thirty years in the U.S. Holstein population as determined by examining pedigrees of sires currently in use. It appears that this genotype has unknowingly been selected for using traditional animal selection. Homozygous and heterozygous animals are found within the Holstein population.

The genotype (α-lac (−13)) has been examined for its correlation with milk and milk protein production. The three additional variations are being examined to determine the frequency of their differences in the cattle population and their correlation with milk and milk protein production. The possible linkage of these genotypes is also being examined using DNA sequencing. The goal of this technology is to identify the optimal regulatory genotype for α-lactalbumin and to select animals with those particular characteristics.

Detection and Selection of Four Genetic Variants

The region of sequence where the α-lac (−13) variation occurs can be amplified using the polymerase chain reaction (PCR) (Sambrook et al., 1989) and two of the following primers which were developed. Each primer allows for amplification of a specific portion of the α-lactalbumin gene. Combinations of the listed primers can be used in between any two of the primer locations listed below.

| Primer No.[<]Tc;;14 (SEQ ID NO:) | Primer sequence (From translation | Primer location start site) |
|---|---|---|
| 1 [ ](12) | 5' CTCTTCCTGGATGTAAGGCTT 3' | (−120)–(−100) |
| 2 [ ](13) | 5' TCCTGGGTGGTCATTGAAAGGACT 3' | (−2000)–(−1975) |
| 3 [ ](14) | 5' CAATGTGGTATCTGGCTATTTAGTG 3' | (−717)–(−692) |
| 4 [ ](15) | 5' AGCCTGGGTGGCATGGAATA 3' | (+53)–(+33) |
| 5 [ ](16) | 5' GAAACGCGGTACAGACCCCT 3' | (+453)–(+433) |

After amplification of the specific region, the DNA is either sequenced or digested with restriction enzymes to detect the sequence differences. In the case of the α-lac (−13) variation, the sequence difference can be seen using the restriction enzyme MnlI (5'CTCC 3' recognition site). The PCR DNA product is digested with MnlI and then run on a 4% NuSieve agarose gel to observe the polymorphism.

A 650 base pair sequence containing all four of the variations is being examined using a unique sequencing technique. PCR is initially used to amplify a 770 base pair portion of the α-lactalbumin 5' flanking region. Another PCR reaction is then performed using a portion of the initial reaction and the following primers (SEQ ID NO:10 and SEQ ID NO:11 respectively):

α-lac seq. 1 5'ACGCTTGTAAAACGACGGCCAGTTGATTCTCAGTCTCTGTGGT 3'
α-lac seq. 2 5'AGCATCAGGAAACAGCTATGACCTGGGTGGCATGGAATAGGAT 3'

The primers listed above contain a portion of the α-lactalbumin gene as well as both M13 DNA sequencing primers. The primers are designed to allow for DNA sequencing to be performed in both directions on the PCR DNA product. The final PCR product will contain the region of α-lactalbumin containing the four genetic variants, the two M13 sequencing priming regions and 5 "dummy bases" on the end to aid in the M13 primer binding.

Figure 8:
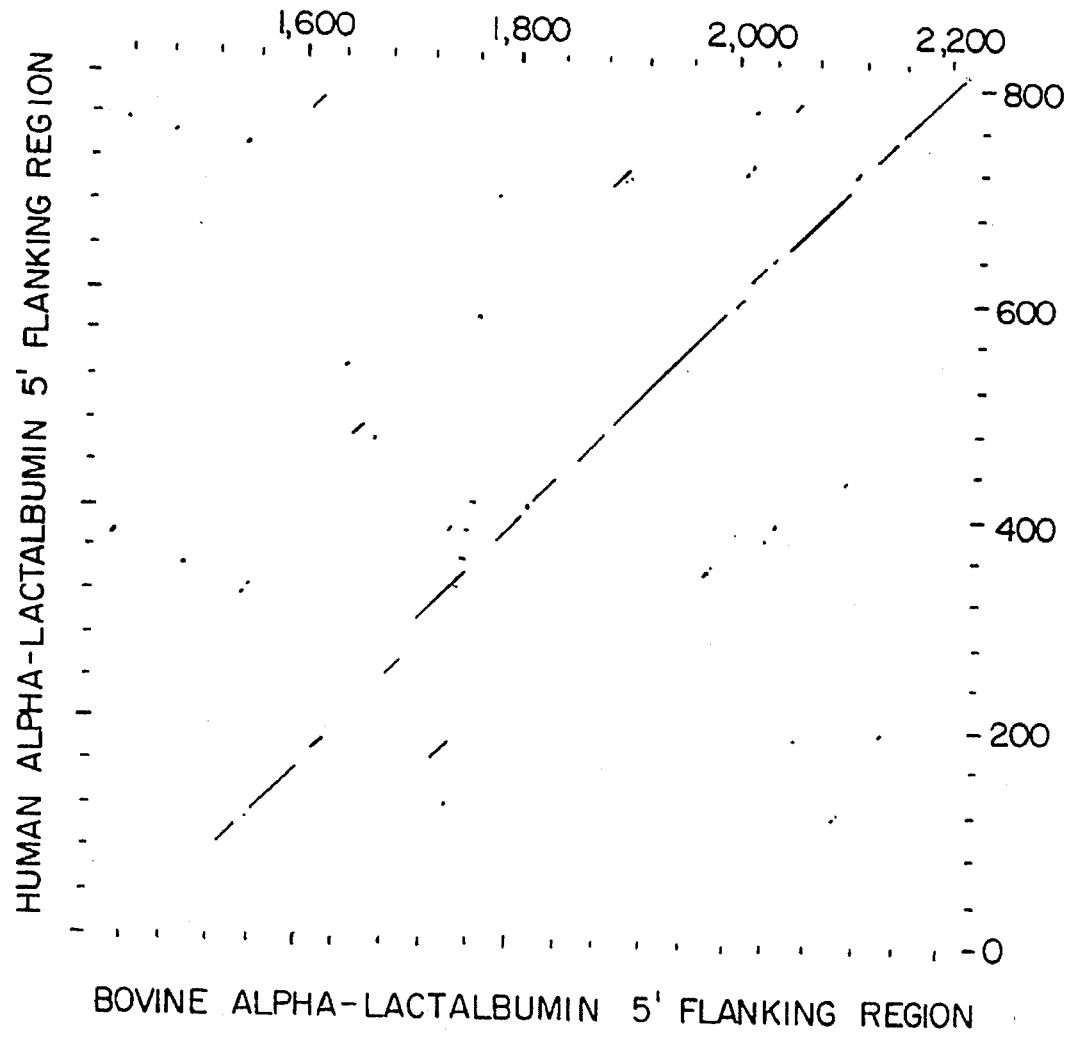
FIG. 8 is a DOTPLOT™ graph comparing the bovine α-lactalbumin 5' flanking sequence to the same region of the human α-lactalbumin sequence.
Figure 9:
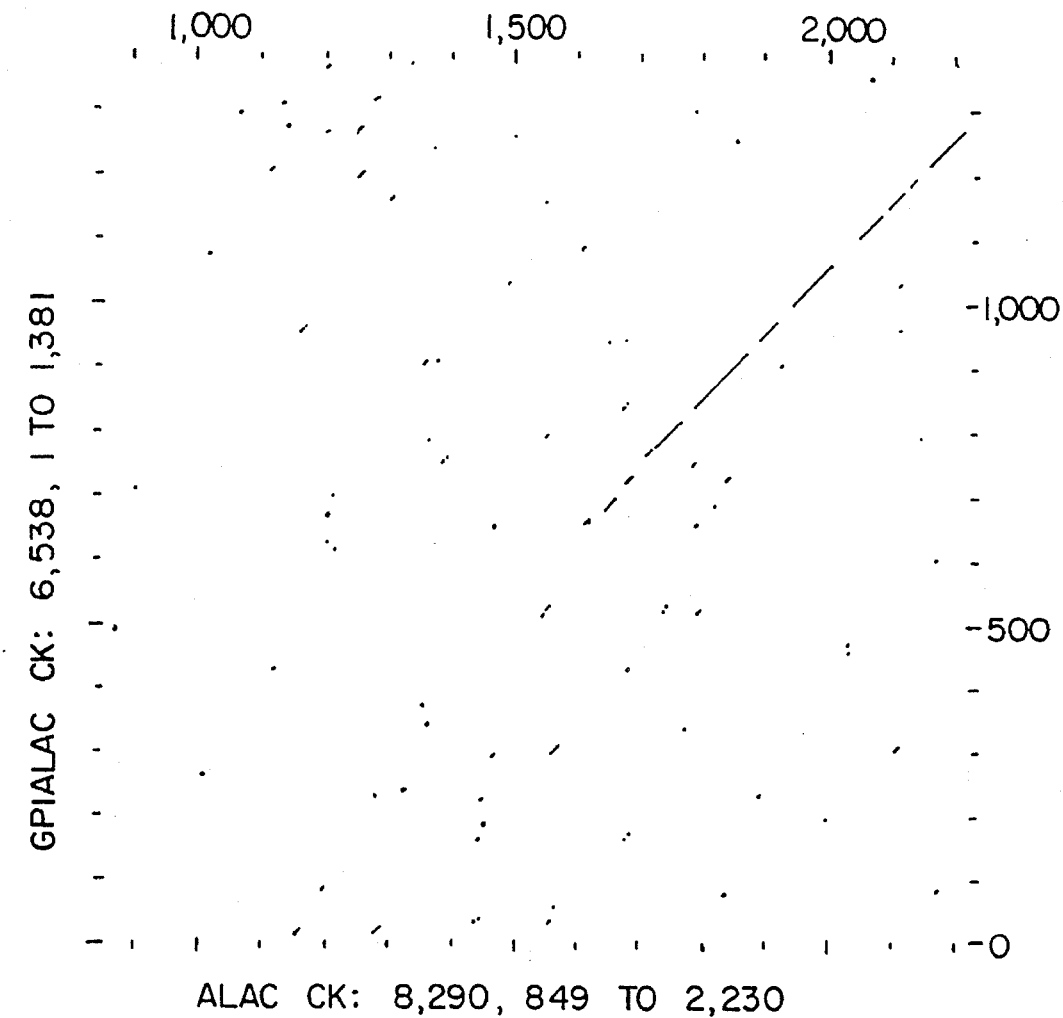
FIG. 9 is a DOTPLOT™ graph comparing the bovine α-lactalbumin 5' flanking sequence to the same region of the guinea pig α-lactalbumin sequence.
Figure 10:
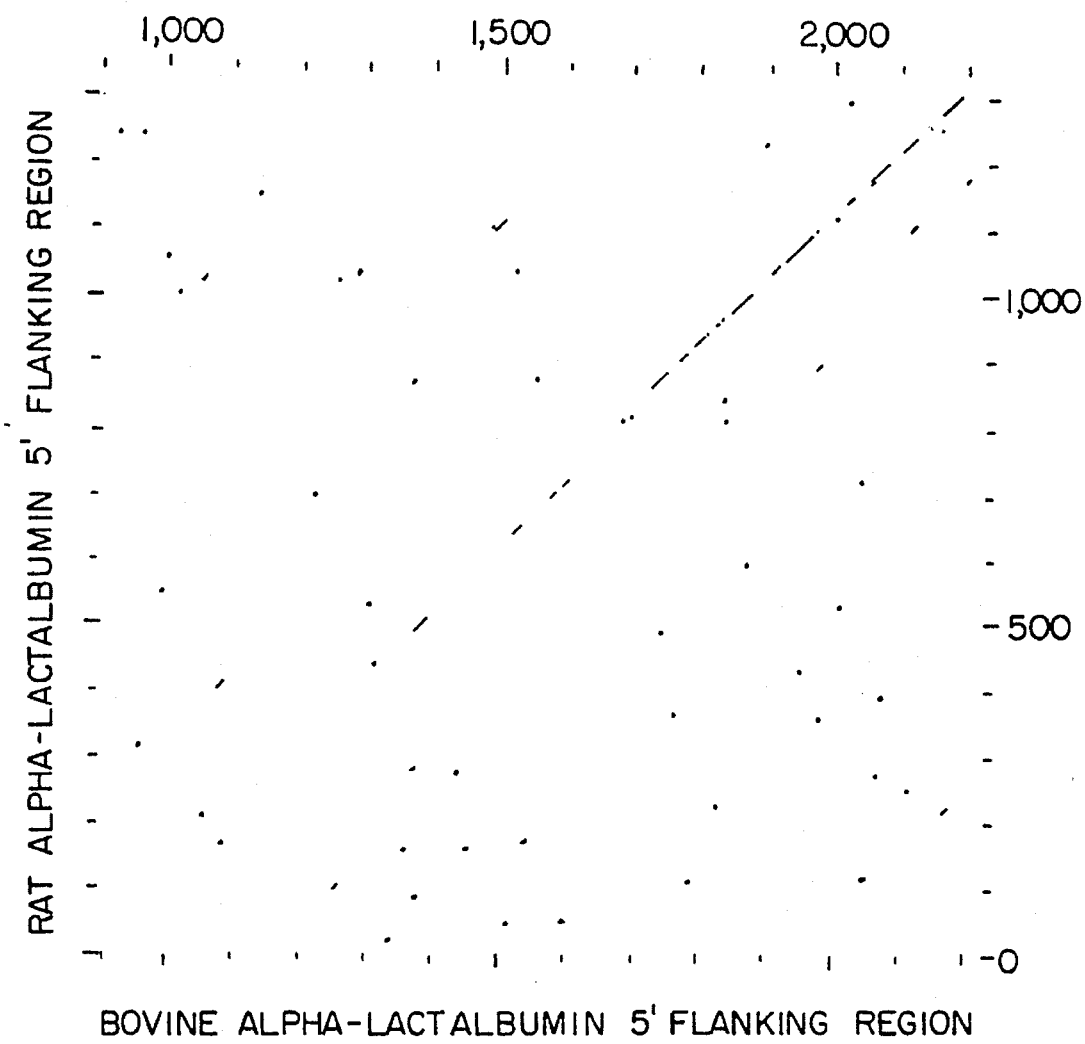
FIG. 10 is a DOTPLOT™ graph comparing the bovine α-lactalbumin 5' flanking sequence to the same region of the rat α-lactalbumin sequence.

Comparison of Highly Conserved Portions of the 5' Flanking Region of α-Lactalbumin Between Species Reference is made to FIGS. 8–10 for DOTBLOT™ graphs comparing the bovine α-lactalbumin sequence to the same region of the human (FIG. 8), guinea pig (FIG. 9), and rat (FIG. 10). The region in FIG. 8 (human) spans 819 base pairs. The sequences are highly conserved to about 700 base pairs. The region in FIG. 9 (guinea pig) spans 1381 base pairs. The sequences are highly conserved to about 700 base pairs, but then diverge. The region in FIG. 10 (rat) spans 1337 base pairs. The sequences are highly conserved to about 700 base pairs, but then diverge. Species differences in control regions would be expected to occur in non conserved regions of the sequence.

Comparison of 5' Flanking Region of Bovine α-Lactalbumin to Other Bovine Milk Protein Genes Portions of the 5' flanking region of the other bovine milk protein genes (as1 and as2 casein, β-casein, K-casein and β-lactoglobulin) which are highly conserved with the α-lactalbumin 5' flanking region were identified. It is probable that sequence differences within these regions will also have an effect on mRNA production as well as final protein production. Two examples of these highly homologous regions are listed below.

The bovine α-lactalbumin sequence from (−161)–(−115) (SEQ ID NO: 17) compared to the bovine β-casein sequence (SEQ ID NO:1B) corresponding to the same region of the gene. Percent similarity is 69% over 46 bases.

```
AGGAAGCTCAATGTTTCTTTGTTGGTTTTACTGGCCTCTCTTGTCA
| | | |  | | |  |  |  | | | |  | |  |  |   | | | | | |  | | | |   | | |
AGGAGGCT. ATTCTTTCCTTTTAGTCTATACTGTCTTCGCTCTTCA
```

The bovine α-lactalbumin sequence (SEQ ID NO:19) (−1545)–(−1485) from the start of the signal peptide coding region is compared to the bovine β-casein sequence (SEQ ID NO:20) corresponding to the same region of the gene. Percent similarity is 75% over 69 bases.

```
TATAAGAAATCAGGCTTTAGAGACTGATGTAGAGAGAATGAGCCCTGGCA
| |  | | | | | | | |   | | | |     |  | | |                         | | |  | | | | |
    TCTCAGAAATCACACTTTTTTGCCTGTG............GCCTTGGCA

TACCAGAAGCTAACAGCTA
              | | | |  | | | | | | | | |   | |
            . ACCAAAAGCTAACACATA
```

The included data indicate that the bovine α-lactalbumin gene will be useful as selection tool in the dairy cattle industry as well as a valuable control/enhancer and gene to be used in the field of genetically engineered mammals. The control region we have cloned contains the necessary regulatory elements to express genes in the milk of genetically engineered mammals as well as the "high expressing genotype" as shown by our milk and milk protein production and sequence variation data. These facts make this a useful gene in both industrial and research areas. Application of these techniques to the other milk proteins will allow for the selection of valuable genotypes corresponding to the β-casein, $as_1$- and $as_2$-casein and K-casein genes and the β-lactoglobulin genes.

Coding Region

The coding region of the α-lactalbumin protein includes a 1.7 kilobase sequence.

3' Flanking Region

The 3' flanking region is an 8.8 kilobase flanking region downstream of the DNA sequence coding for the desired recombinant protein. This region apparently stabilizes the RNA transcript of the expression system and thus increases the yield of desired protein from the expression system.

Operation

The above-described expression systems may be prepared by methods well-known in the art. Examples include various ligation techniques employing conventional linkers, restriction sites, etc. Preferably, these expression systems are part of larger plasmids.

After isolation and purification, the expression systems or constructs are added to the gene pool which is to be genetically altered.

The methods for genetically engineering mammals are well-known to the art. Reference is made to to Alberts, B. et al., 1989 and Lewin, B. 1990, for textbook descriptions of genetic engineering and transgenic alteration of animals. Briefly, genetic engineering involves the construction of expression vectors so that a cDNA clone or genomic structure is connected directly to a DNA sequence that acts as a strong promoter for DNA transcription. By means of genetic engineering, mammalian cells, such as mammary tissue, can be induced to make vast quantities of useful proteins.

For the purposes of this invention, the term "genetic engineering," as defined supra. in the list of definitions, includes single line alteration, i.e., genetic alteration only during the life of the affected animal with no germ line permanence. The construct can be genetically incorporated in mammalian glands such as mammary glands and mammalian stem cells.

Genetic engineering also includes transgenic alteration, i.e., the permanent insertion of the gene sequence into the genomic structure of the affected animal and any offspring. Transgenically altering a mammal involves microinjecting a DNA construct into the pronuclei of the fertilized mammalian egg to cause one or more copies of the construct to be retained in the cells of the developing mammal. In a transgenic animal, the engineered genes are permanently inserted into the germ line of the animal.

The genetically engineered mammal is then characterized by an expression system comprising the α-lactalbumin control region operatively linked to an exogenous DNA sequence coding for the recombinant protein through a DNA sequence coding for a signal peptide effective in secreting and maturing the recombinant protein in mammary tissue. In order to produce and secrete the recombinant protein into the mammal's milk, the transgenic mammal must be allowed to produce the milk, after which the milk is collected. The milk may then be used in standard manufacturing processes. The exogenous recombinant protein may also be isolated from the milk according to methods known to the art.

Selection Characteristics

The α-lactalbumin control/enhancer sequence of FIG. 1 is also important as a selection characteristic for identifying superior or elite milk producing mammals. Presently, those in the dairy cattle business can only rely on pedigree information, which is frequently not available, to predict milk and milk protein production in mammals, specifically the bovine species. The study of physiological markers as a means for determining milk and milk protein production has received some interest. The most common physiological marker traits studied in dairy cattle are hormones, enzymes, and different blood metabolites. Components of the immune system have also been studied. Traits listed as possible marker traits for milk yield include thyroxine, blood urea nitrogen, growth hormones, insulin-like growth factors and insulin, and glucose and free fatty acids. While these techniques have shown some advances in predicting milk and milk protein production in a dairy animal, there is currently no other reliable means to predict these characteristics.

The present invention provides a selection characteristic for identifying superior milk and milk protein-producing mammals comprising inherited genetic material which is DNA occurring in the genetic structure of the mammal in which the genetic material encodes a dominant selectable marker for bovine α-lactalbumin.

The DNA sequence disclosed herein serves as a characteristic marker for elite milk producing mammals.

The examples below describe the invention disclosed herein, although the invention is not to be understood as limited in any way to the terms and scope of the examples.

EXAMPLES

Example 1: α-lac (−13) variation study

Forty-two mammals were selected in a stratified random manner to provide mammals of a wide range of milk and milk protein production capabilities within the UW herd.

DNA was isolated according to procedures known to the art from a random sample of 42 Holstein dairy cows in the University of Wisconsin-Madison herd. Each mammal was genotyped as described previously for the α-lactalbumin (−13) variation using a 4% NuSieve gel of MnlI digested PCR products.

Figure 12:
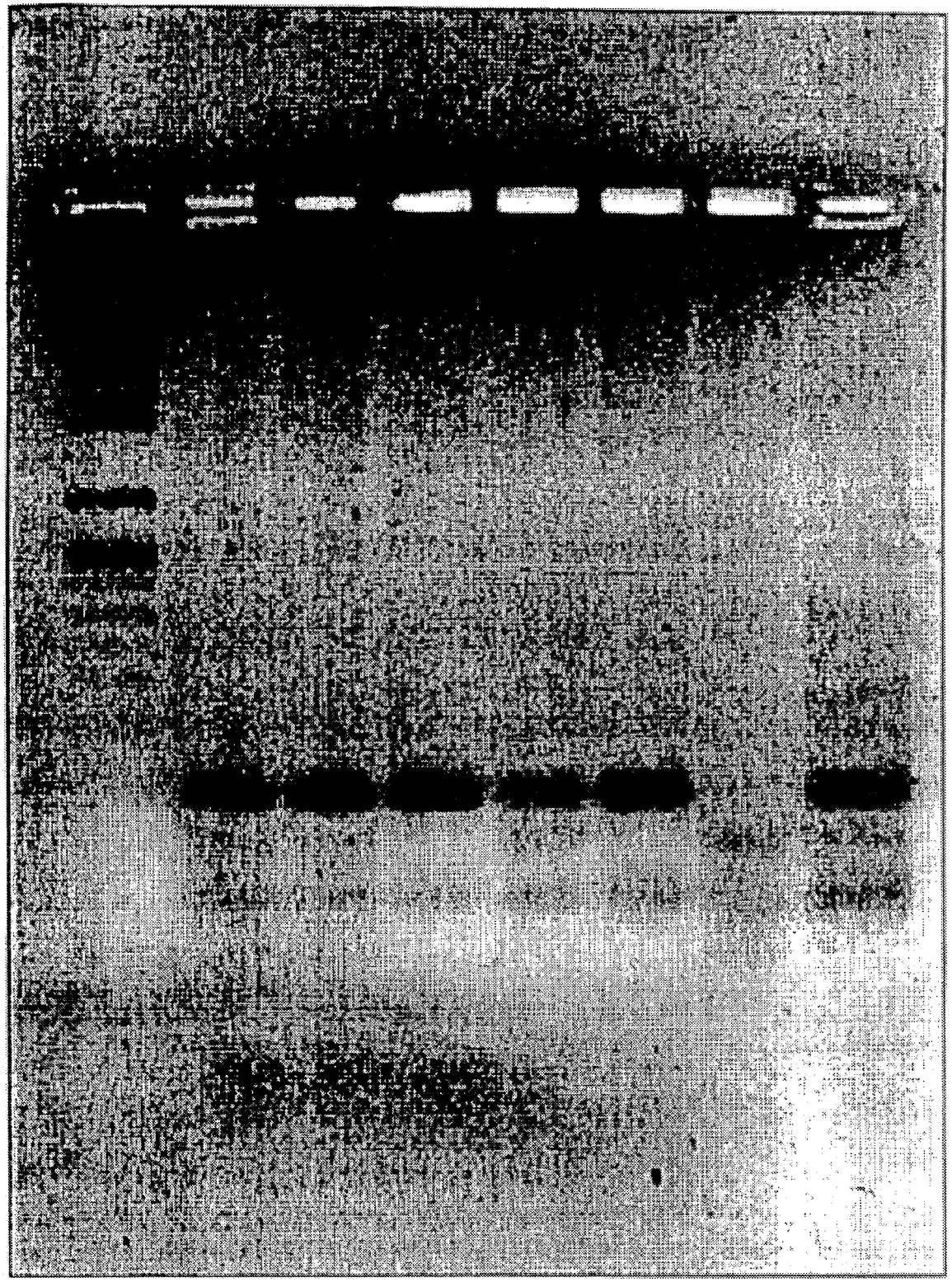
FIG. 12 is a 4% NuSieve autoradiographic gel of MnII digested PCR products.

The gene frequency in this population is 28% for the α-lac (−13) A and 72% for the α-lac (−13) B. Each of the distinct genotypes are shown on the gel in FIG. 12. The legend for the gel of FIG. 12 is as follows:

| Lane 1 | Molecular Weight Standards | |
|---|---|---|
| Lane 2–3 | heterozygous | α-lac (−13) AB |
| Lane 4: | homozygous | α-lac (−13) BB |
| Lane 5 | heterozygous | α-lac (−13) AB |
| Lane 6 | homozygous | α-lac (−13) BB |
| Lane 7 | homozygous | α-lac (−13) AA |
| Lane 8 | heterozygous | α-lac (−13) AB |

Figure 13:
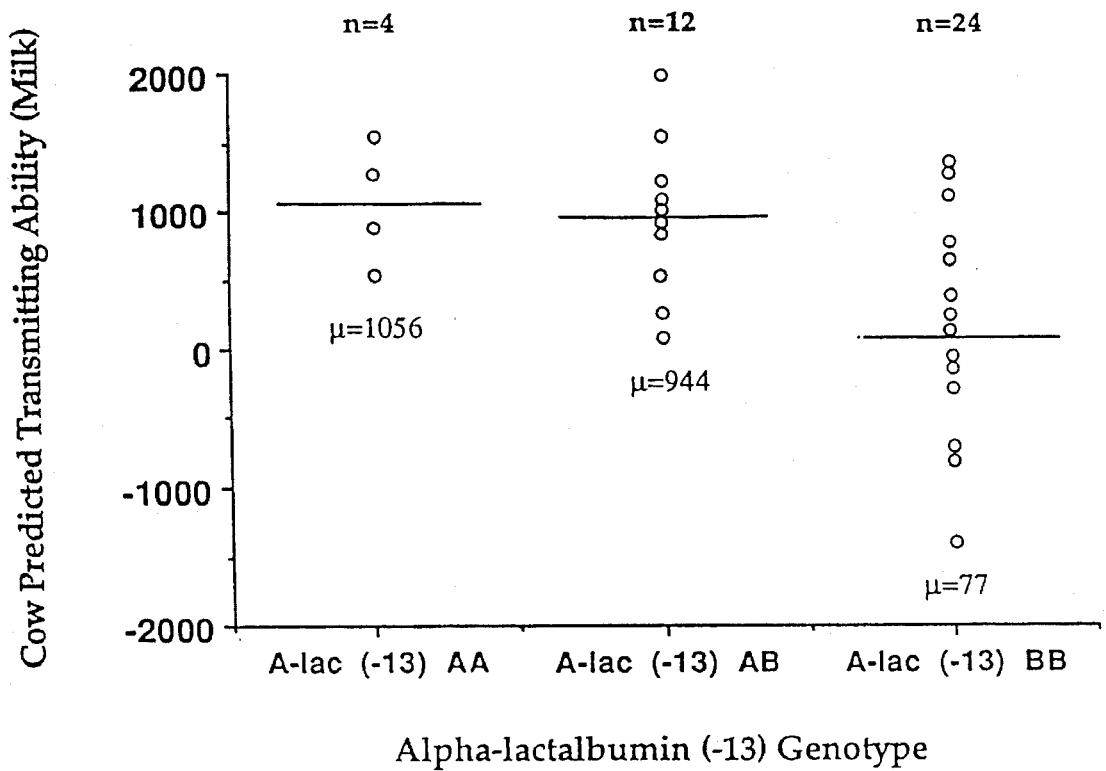
FIG. 13 is a graph illustrating a scatter plot of each data point in FIG. 12 as well as mean values for each of the three genotypes.

Analysis of the genetic capabilities of the 42 mammals indicates a possible major gene effect caused by the α-lac (−13) allele or linked to the α-lac (−13) allele. A scatter plot of each data point as well as mean values for each of the three genotypes is illustrated in FIG. 13. Holstein cows were compared using their predicted transmitting ability for milk.

The data indicate that the α-lac (−13)A genotype is the preferred genotype for milk and milk protein production. Table 1 shown below indicates the statistical association of differences in milk and milk protein production ability observed between each of the genotypes for the traits listed below. Analysis of variance and T tests (LSD) were performed on the data. All of the production yield traits were positively correlated with the α-lac (−13) A allele. Milk protein percentage was negatively correlated to the α-lac (−13) A allele.

TABLE 1

| | Genotype | | |
|---|---|---|---|
| Trait/Genotype | α-lac (−13) AA | α-lac (−13) AB | α-lac (−13) BB |
| PTA (Milk) /AA | — | N.S. | p < 0.02 |
| PTA (Milk)/AB | N.S. | — | p < 0.02 |
| ME305 (Milk)/AA | — | N.S. | N.S. |
| ME305 (Milk)/AB | N.S. | — | p < 0.1 |
| PTA (Protein #)/AA | — | N.S. | N.S. |
| PTA (Protein #)/AB | N.S. | — | P < 0.1 |
| PTA (Protein %)/AA | — | N.S. | p < 0.01 |
| PTA (Protein %)/AB | N.S. | — | p < 0.01 |

Example 2. Production of Transgenic mice to study the regulation of bovine α-lactalbumin gene expression Genomic Library Screening:

The gene encoding the milk protein bovine α-lactalbumin was isolated from a bovine genomic library (Woychik, 1982). The genomic library was screened according to the following procedure. Approximately 1.5 million lambda plaques were transferred to nylon membranes using procedures described by Maniatis et al. (1989). The α-lactalbumin cDNA (Hurley, 1987) or a 770 base pair PCR product was nick translated (BRL) with a-P32 labeled dCTP. Blots were prehybridized overnight (65C) then hybridized for 16 hours at 65C. Blots were washed (Twice in 2X SSC 1% SDS, Once in 0.1X SSC 0.1% SDS) at 65C and placed on Kodak X-OMAT film for autoradiography. A 8.0 kilobase fragment containing the α-lactalbumin gene was purified as illustrated in FIG. 4. The 8.0 kilobase fragment contained 2.1 kilobases of 5' flanking region, the 1.7 kilobase coding region and 2.6 kilobases of 3' flanking region.

Production of transgenic mice:

- Mature C57B6 X DBA2J F1 (B6D2) female were superovulated (PMSG and hCG) and mated with ICR or B6D2 males to yield fertilized eggs for pronuclear microinjection. The eggs were microinjected using a Leitz micromanipulator and a Nikon inverted microscope. Forty normal appearing two cell embryos were transferred to each pseudopregnant recipient (University of Wisconsin-Madison Biotechnology Center Transgenic Mouse Facility, Dr. Jan Heideman).

Screening of transgenic mice using PCR:

Tail DNA was extracted using the method described by Constantini et al. (1986). Polymerase chain reaction (PCR) was performed using 10 ml 10x PCR reaction buffer (Promega Corp., Madison, WI.), 200 mM each dNTP (Pharmacia Intl., Milwaukee, WI,), 1.0 μm each primer (upstream primer 25mer −712 to −687 (5' CAATGTGGTATCTGGC-TATTTAGTG 3') (SEQ ID NO:14), downstream primer 20mer +39 to +59 (5'AGCCTGGGTGGCATGGAATA 3') (SEQ ID NO:15), 1 unit Taq DNA polymerase (Promega Corp., Madison, WI.) and 1 mg genomic DNA. Volume was adjusted to 100 ml with double distilled sterile water and reaction was overlaid with heavy mineral oil. Samples were subjected to 30 cycles (94C 2 min., 50C 1.5 min., 2C 1.5 min.). Products were run in an 1% agarose gel and stained with ethidium bromide.

Figure 11:
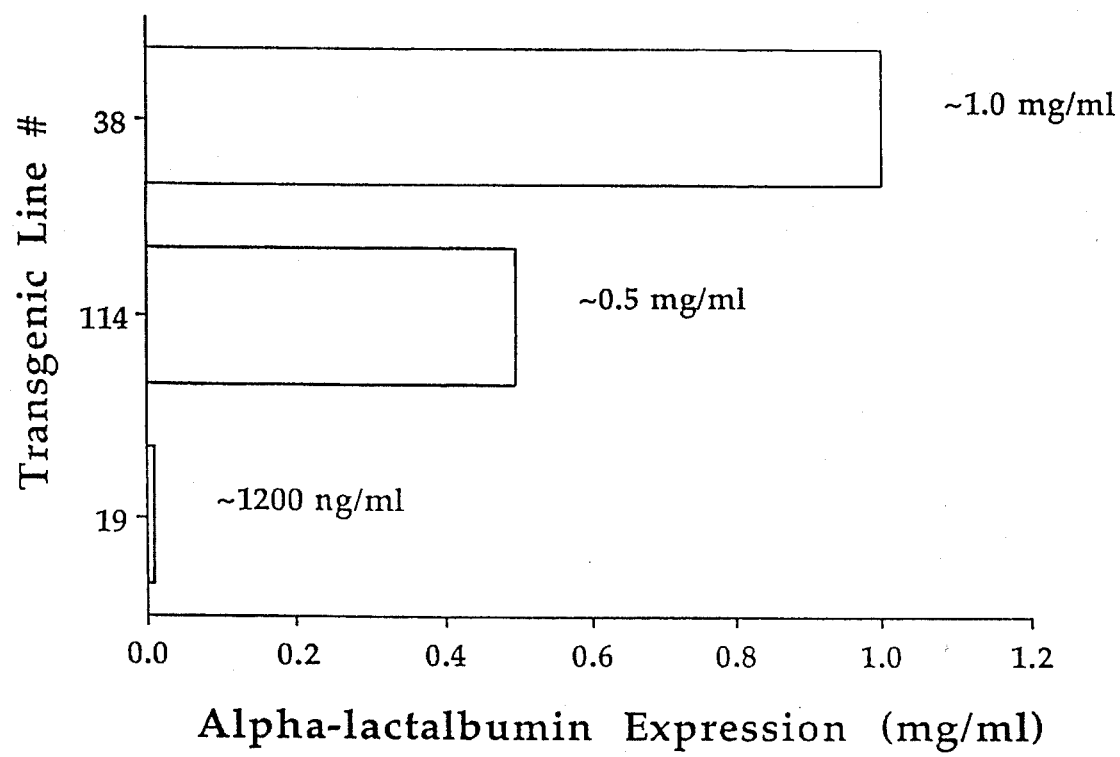
FIG. 11 is a graph illustrating expression levels observed in each of three α-lactalbumin transgenic mouse line.

Mouse Milking:

The mice were separated from their litters for four hours and then anesthetized (0.01 ml/g body weight I.P. injection of 36% propylene glycol, 10.5% ethyl alcohol (95%), 41.5% sterile water, and 12% sodium pentabarbitol (50 mg/ml)). After being anesthetized the mice were injected I.M. with 0.3 I.U. oxytocin and milked using a small vacuum milking machine. Three of fifty-one live offspring were identified as being transgenic using polymerase chain reaction. Reference is made to FIG. 11 for a graph illustrating expression levels observed in each of the 3 α-lactalbumin transgenic mouse line.

ELISA:

Second generation mammals from one line were milked and analysis was performed using an ELISA (enzyme linked immunosorbent assay) for bovine α-lactalbumin according to the following procedure:

1. Coat 1/40k bovine α-lactalbumin antiserum 100 ml per well (in 0.05M carbonate buffer, pH 9.6) on Nunc-Immuno Plate IF MaxiSorp.
2. Wash 4x with wash buffer (0.025% Tween 20 in PBS pH 7.2)
3. Add 50 ml assay buffer (0.04M MOPS, 0.12M NaCl, 0.01M EDTA, 0.1% gelatin, 0.05% Tween 20, 0.005% chlorhexidine digluconate, Leupeptin 50 mg/ml, pH 7.4).
4. Add 50 ml of standards and samples (in assay buffer) in triplicate.

Add 50 ml 1/100k diluted α-lactalbumin biotin conjugate.

6. Incubate overnight at 4C
7. Wash 4x with wash buffer
8. Add 100 ml 1/10k assay buffer diluted ExtrAvidin-peroxidase (Sigma). Incubate 2 hours at RT.
9. Wash 4x twice with wash buffer.
10. Add 125 ml fresh substrate buffer (200 ml tetramethylbenzidine 20 mg/ml) DMSO, 64 ml 0.5M hydrogen peroxide, 19.74 ml sodium acetate, pH 4.8).
11. Incubate for 12 minutes at RT.
12. Add 50 ml 0.5M sulfuric acid to stop substrate reaction.
13. Read absorbance at 450 nm minus 600 nm in an EIA autoreader.

Bovine α-lactalbumin was present at a concentration of levels up to and beyond 1.0 mg/ml mouse milk. Expression was determined by Western Blotting in the following steps. The 14% PAGE gel was transfered to an Immobilon-P membrane (Millipore), which was blocked in 0.02 M sodiumphosphate, 0.12M NaCl, 0.01% gelatin, 0.05% Tween 20, pH=7.2, and incubated with anti-bovine α-lactalbumin (1/2000 dilution) for 2 hours at room temperature. The gel was washed twice (2 min.) with an ELISA wash buffer and incubated with goat anti-rabbit IgG-HRP for 2 hours at room temperature, followed by washing 3 times with a wash buffer and washing once with double-distilled water. The gel was placed in a substrate solution (25 mg 3,3'-diaminobenzidine, 1 ml 1% $CoCl_2$ in $H_2O$, 49 ml PBS pH 7.4 and 0.05 ml 30% $H_2O_2$) and monitored for color development. The membrane was air dried.

It is understood that the invention is not confined to the particular constructions and arrangements herein illustrated and described, but embraces such modified forms thereof as come within the scope of the claims following the bibliography.

BIBLIOGRAPHY OF CITED REFERENCES

Akers, R. M. et al., 1981, "Prolactin regulation of milk secretion and biochemical differentiation of mammary epithelial cells in periparturient cows." Endocrinology, 109:23.

Alberts, B. et al., 1989, *Molecular Biology of The Cell* (Second Edition), Garland Publishing, Inc., New York, pp. 265–271.

Bonsing, J. et al., 1988, "Complete nucleotide sequence of the bovine beta-casein gene," *Aust. J. Biol. Sci.*, 41: 527–537.

Brew, K. and R. L. Hill, 1975, "Lactose biosynthesis." *Rev. Physiol. Biochem. Pharmacol.*, 72:105.

Eigel, W.N. et al., 1984, "Nomenclature of proteins of cow's milk: fifth revision." *J. Dairy Sci.*, 67:1599.

Goodman, G. T. et al., 1983, "Hormonal regulation of alpha-lactalbumin secretion from bovine mammary tissue cultured in vitro." *Endocrinology*, 112:1324.

Hall, L , et al , 1987, . "Organization and sequence of the human α-lactalbumin and the origins of lactation," *Biochem. J.*, 242: 735–742.

Hurley, W. L. and L. A. Schuler, 1987, "Molecular cloning and nucleotide sequence of a bovine α-lactalbumin cDNA," *Gene* 61: 119–122.

Larson, B. L., 1985, "Biosynthesis and cellular secretion of milk." In: *Lactation*, pp. 129–163, edited by B. L. Larson, The Iowa State University Press, Ames.

Lewin, B., 1990, *GENES IV*, Oxford University Press, New York, pp. 691–702.

McFadden, T.B. et al., 1987, "Alpha-lactalbumin in bovine serum: relationships with udder development and function." *J. Dairy Sci.*, 70:259.

Sambrook, J. et al., 1989, *Molecular Cloning–A Laboratory Manual* (Second Edition), Cold Spring Harbor Laboratory Press.

Vilotte, J et al , 1987, "Complete nucleotide sequence of bovine α-lactalbumin gene: comparison with its rat counterpart. *Biochimie*, 69: 609–620.

Woychik, R., et al., *Nucl. Acids Res.*, 10:7197–7210 (1982).

---

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 26 base pairs
( B ) TYPE: nucleic acid
( C ) STRANDEDNESS: single (D) TOPOLOGY: linear (ii) MOLECULE TYPE: DNA (genomic)

(xi) SEQUENCE DESCRIPTION: SEQ ID NO:1:

| ATGACCATGA | TTACGAATTC | ATCGTA | | | | 26 |

(2) INFORMATION FOR SEQ ID NO:2:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

| GAACAGTTAT | CTAGATCTCG | AGCTCGCGAA | AGCTTGCATG | CCTGCAGGTC | GACTCTAGAG | 60 |
| GATCCCCGGG | TACCGAGCTC | GAATTCAC | | | | 88 |

(2) INFORMATION FOR SEQ ID NO:3:

(i) SEQUENCE CHARACTERISTICS:
        (A) LENGTH: 2044 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: signal peptide coding region
        (B) LOCATION: 1943..2043

(ix) FEATURE:
        (A) NAME/KEY: inherited control region for a-lactalbumin
        (B) LOCATION: 1966

(ix) FEATURE:
        (A) NAME/KEY: putative steroid response element
        (B) LOCATION: 1433..1446

(ix) FEATURE:
        (A) NAME/KEY: RNA polymerase binding region
        (B) LOCATION: 1961..1978

(xi) SEQUENCE DESCRIPTION: SEQ ID NO:3:

| GATCAGTCCT | GGGTGGTCAT | TGAAAGGACT | GATGCTGAAG | TTGAAGCTCC | AATACTTTGG | 60 |
| CCACCTGATG | CGAAGAACTG | ACTCATGTGA | TAAGACCCTG | ATACTGGGAA | AGATTGAAGG | 120 |
| CAGGAGGAGA | AGGGATGACA | GAGGATGGAA | GAGTTGGATG | GAATCACCAA | CTCGATGGAC | 180 |
| ATGAGTTTGA | GCAAGCTTCC | AGGAGTTGGT | AATGGGCAGG | GAAGCCTGGC | GTGCTGCAGT | 240 |
| CCATGGGGTT | GCAAAGAGTT | GGACACTACT | GAGTGACTGA | ACTGAACTGA | TAGTGTAATC | 300 |
| CATGGTACAG | AATATAGGAT | AAAAAGAGG | AAGAGTTTGC | CCTGATTCTG | AAGAGTTGTA | 360 |
| GGATATAAAA | GTTTAGAATA | CCTTTAGTTT | GGAAGTCTTA | AATTATTTAC | TTAGGATGGG | 420 |
| TACCCACTGC | AATATAAGAA | ATCAGGCTTT | AGAGACTGAT | GTAGAGAGAA | TGAGCCCTGG | 480 |
| CATACCAGAA | GCTAACAGCT | ATTGGTTATA | GCTGTTATAA | CCAATATATA | ACCAATATAT | 540 |
| TGGTTATATA | GCATGAAGCT | TGATGCCAGC | AATTTGAAGG | AACCATTTAG | AACTAGTATC | 600 |
| CTAAACTCTA | CATGTTCCAG | GACACTGATC | TTAAAGCTCA | GGTTCAGAAT | CTTGTTTTAT | 660 |
| AGGCTCTAGG | TGTATATTGT | GGGGCTTCCC | TGGTGGCTCA | GATGGTAAAG | TGTCTGCCTG | 720 |
| CAATGTGGGT | GATCTGGGTT | CGATCCCTGG | CTTGGGAAGA | TCCCCTGGAG | AAGGAAATGG | 780 |

| | | | | | |
|---|---|---|---|---|---|
| CAACCCACTC | TAGTACTCTT | ACCTGGAAAA | TTCCATGGAC | AGAGGAGCCT | TGTAAGCTAC | 840 |
| AGTCCATGGG | ATTGCAAAGA | GTTGAACACA | ACTGAGCAAC | TAAGCACAGC | ACAGTACAGT | 900 |
| ATACACCTGT | GAGGTGAAGT | GAAGTGAAGG | TTCAATGCAG | GGTCTCCTGC | ATTGCAGAAA | 960 |
| GATTCTTTAC | CATCTGAGCC | ACCAGGGAAG | CCCAAGAATA | CTGGAGTGGG | TAGCCTATTC | 1020 |
| CTTCTCCAGG | GGATCTTCCC | ATCCCAGGAA | TTGAACTGGA | GTCTCCTGCA | TTTCAGGTGG | 1080 |
| ATTCTTCACC | AGCTGAACTA | CCAGGTGGAT | ACTACTCCAA | TATTAAAGTG | CTTAAAGTCC | 1140 |
| AGTTTTCCCA | CCTTTCCCAA | AAAGGTTGGG | TCACTCTTTT | TTAACCTTCT | GTGGCCTACT | 1200 |
| CTGAGGCTGT | CTACAAGCTT | ATATATTTAT | GAACACATTT | ATTGCAAGTT | GTTAGTTTTA | 1260 |
| GATTTACAAT | GTGGTATCTG | GCTATTTAGT | GGTATTGGTG | GTTGGGGATG | GGGAGGCTGA | 1320 |
| TAGCATCTCA | GAGGGCAGCT | AGATACTGTC | ATACACACTT | TTCAAGTTCT | CCATTTTTGT | 1380 |
| GAAATAGAAA | GTCTCTGGAT | CTAAGTTATA | TGTGATTCTC | AGTCTCTGTG | GTCATATTCT | 1440 |
| ATTCTACTCC | TGACCACTCA | ACAAGGAACC | AAGATATCAA | GGGACACTTG | TTTTGTTTCA | 1500 |
| TGCCTGGGTT | GAGTGGGCCA | TGACATATGA | TGATGTACAG | TCCTTTTCCA | TATTCTGTAT | 1560 |
| GTCTCTAAGA | GGAAGGAGGA | GTTGGCCGTG | GACCCTTTGT | GCATTTCTG | ATTGCTTCAC | 1620 |
| TTGTATTACC | CCTGAGGCCC | CCTTTGTTCC | TGAAATAGGT | TGGGCACATC | TTGCTTCCTA | 1680 |
| GAACCAACAC | TACCAGAAAC | AACATAAATA | AAGCCAAATG | GGAAACAGGA | TCATGTTTGT | 1740 |
| AACACTCTTT | GGGCAGGTAA | CAATACCTAG | TATGGACTAG | AGATTCTGGG | GAGGAAAGGA | 1800 |
| AAAGTGGGGT | GAAATTACTG | AAGGAAGCTC | AATGTTCTT | TGTTGGTTTT | ACTGGCCTCT | 1860 |
| CTTGTCATCC | TCTTCCTGGA | TGTAAGGCTT | GATGCCAGGG | CCCCTAAGGC | TTTTTCCACA | 1920 |
| AATAAAGGA | GGTGAGCAGT | GTGGTGACCC | CATTTCAGAA | TCTTGAGGGG | TAACCAAAAT | 1980 |
| GATGTCCTTT | GTCTCTCTGC | TCCTGGTAGG | CATCCTATTC | CATGCCACCC | AGGCTGAACA | 2040 |
| GTTA | | | | | | 2044 |

( 2 ) INFORMATION FOR SEQ ID NO:4:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CATATTCTAT TCTA 14

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CATATTCTAT TCCTA 15

( 2 ) INFORMATION FOR SEQ ID NO:6:

( i ) SEQUENCE CHARACTERISTICS:
        ( A ) LENGTH: 15 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:6:

CATATTCTAT TTCTA                                                    15

(2) INFORMATION FOR SEQ ID NO:7:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:7:

TCTTGAGGGG TAACCAAA                                                 18

(2) INFORMATION FOR SEQ ID NO:8:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:8:

TCTTGGGGGT AGCCAAA                                                  17

(2) INFORMATION FOR SEQ ID NO:9:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:9:

TCTTGGGGGG TCACCAAA                                                 18

(2) INFORMATION FOR SEQ ID NO:10:

(i) SEQUENCE CHARACTERISTICS:
       (A) LENGTH: 43 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:10:

ACGCTTGTAA AACGACGGCC AGTTGATTCT CAGTCTCTGT GGT                     43

(2) INFORMATION FOR SEQ ID NO:11:

(i) SEQUENCE CHARACTERISTICS:
       (A) LENGTH: 43 base pairs
       (B) TYPE: nucleic acid
       (C) STRANDEDNESS: single
       (D) TOPOLOGY: linear (ii) MOLECULE TYPE: DNA (genomic)

( x i ) SEQUENCE DESCRIPTION: SEQ ID NO:11:

AGCATCAGGA AACAGCTATG ACCTGGGTGG CATGGAATAG GAT 43

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CTCTTCCTGG ATGTAAGGCT T 21

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

TCCTGGGTGG TCATTGAAAG GACT 24

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CAATGTGGTA TCTGGCTATT TAGTG 25

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

AGCCTGGGTG GCATGGAATA 20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

GAAACGCGGT ACAGACCCCT 20

( 2 ) INFORMATION FOR SEQ ID NO:17:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

AGGAAGCTCA ATGTTTCTTT GTTGGTTTTA CTGGCCTCTC TTGTCA      46

( 2 ) INFORMATION FOR SEQ ID NO:18:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

AGGAGGCTAT TCTTTCCTTT TAGTCTATAC TGTCTTCGCT CTTCA      45

( 2 ) INFORMATION FOR SEQ ID NO:19:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

TATAAGAAAT CAGGCTTTAG AGACTGATGT AGAGAGAATG AGCCCTGGCA TACCAGAAGC      60

TAACAGCTA      69

( 2 ) INFORMATION FOR SEQ ID NO:20:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

TCTCAGAAAT CACACTTTTT TGCCTGTGGC CTTGGCAACC AAAAGCTAAC ACATA      55

---

What is claimed is: 1. An isolated DNA sequence comprising the bovine α-lactalbumin 5' flanking region regulatory sequence of SEQ ID NO:3, wherein the sequence contains an adenine at position −13 from the start of the signal peptide coding region. 2. An expression vector comprising the DNA sequence of claim 1. 3. An expression system comprising operatively linked in 5' to 3' order: the bovine α-lactalbumin 5' flanking region regulatory sequence of SEQ ID NO:3, approximately 100 base pairs of the bovine β-casein 5' flanking region, a DNA sequence encoding a protein of interest and the bovine β-casein polyadenylation site. 4. An expression system comprising operatively linked in 5' to 3' order: the bovine α-lactalbumin 5' flanking region regulatory sequence of SEQ ID NO:3 and approximately 8.6 kb of DNA sequence encoding bovine β-casein, which includes the bovine β-casein polyadenylation site. 5. A female transgenic mouse which has inserted into its genome a DNA construct which comprises an exogenous DNA sequence encoding a protein of interest operatively linked to the bovine α-lactalbumin 5' flanking region regulatory sequence of SEQ ID NO:3, wherein expression of said DNA sequence results in the secretion of the protein of interest into the milk of the mouse in recoverable quantities. 6. A female transgenic mouse which has inserted into its genome a DNA construct which comprises a DNA sequence encoding bovine α-lactalbumin operatively linked to the bovine α-lactalbumin 5' flanking regionsregulatory sequence of SEQ ID NO:3, wherein expression of said DNA sequence results in the secretion of bovine α-lactalbumin into the milk of the mouse in recoverable quantities.

7. A process for producing bovine α-lactalbumin in the milk of a transgenic mouse comprising:

a. expressing a DNA construct comprising the following elements operatively linked in 5' to 3' order: the bovine α-lactalbumin 5' flanking region regulatory sequence of SEQ ID NO:3 and a DNA sequence encoding bovine α-lactalbumin, which results in the production of bovine α-lactalbumin in the milk of a mouse;

b. collecting the milk; and c. isolating the bovine α-lactalbumin from the milk.

* * * * *